United States Patent
Wang

(10) Patent No.: US 9,545,430 B2
(45) Date of Patent: Jan. 17, 2017

(54) SIRAITIAE FRUCTUS PRODUCT AND PREPARATION METHOD THEREOF

(71) Applicant: Qingyang Wang, Guilin (CN)

(72) Inventor: Qingyang Wang, Guilin (CN)

( * ) Notice: Subject to any disclaimer, the term of this patent is extended or adjusted under 35 U.S.C. 154(b) by 305 days.

(21) Appl. No.: 14/378,851

(22) PCT Filed: Feb. 17, 2013

(86) PCT No.: PCT/CN2013/071618
§ 371 (c)(1),
(2) Date: Aug. 14, 2014

(87) PCT Pub. No.: WO2013/123864
PCT Pub. Date: Aug. 29, 2013

(65) Prior Publication Data
US 2016/0015764 A1    Jan. 21, 2016

(30) Foreign Application Priority Data
Feb. 23, 2012 (CN) .......................... 2012 1 0041932

(51) Int. Cl.
*A01N 65/00* (2009.01)
*A61K 36/42* (2006.01)
*A61K 31/704* (2006.01)

(52) U.S. Cl.
CPC .............. *A61K 36/42* (2013.01); *A23L 33/105* (2016.08); *A61K 31/704* (2013.01); *A23V 2002/00* (2013.01)

(58) Field of Classification Search
CPC ...................................................... A61K 36/00
USPC ......................................................... 424/725
See application file for complete search history.

(56) References Cited

FOREIGN PATENT DOCUMENTS

| CN | 1860920 A   | 11/2006 |
|----|-------------|---------|
| CN | 101233877 A | 8/2008  |
| CN | 102578565 A | 7/2012  |
| CN | 102578573 A | 7/2012  |

OTHER PUBLICATIONS

Chen, Xuehan. Tea Therapy of Luohanguo. Food and Health. Jun. 2007, No. 6, p. 33.
International Search Report for corresponding International Application No. PCT/CN2013/071618, May 23, 2013, 6 pages.

*Primary Examiner* — Michael Meller
(74) *Attorney, Agent, or Firm* — Mintz Levin Cohn Ferris Glovsky and Popeo, P.C.; Christopher R. Cowles

(57) ABSTRACT

This invention relates to a Siraitiae fructus product and a method for preparing the same. The product uses a Siraitiae fructus seed as a carrier, and Siraitiae fructus flesh is coated on the carrier. The flesh may the original flesh tissue, or flesh pulp prepared through a physical method. The product is convenient for eating, and has a distinct flavor and a high amount of active ingredients. The preparation method is simple and practical, and significantly reduces energy consumption.

1 Claim, 3 Drawing Sheets

SIRAITIAE FRUCTUS PRODUCT AND PREPARATION METHOD THEREOF

This application is the U.S. national phase, pursuant to 35 U.S.C. §371, of PCT international application Ser. No. PCT/CN2013/071618, filed Feb. 17, 2013, designating the United States and published in Chinese on Aug. 29, 2013 as publication WO 2013/123864 A1, which claims priority to Chinese Application Ser. No. 201210041932.1, filed Feb. 23, 2012. The entire contents of the aforementioned patent applications are incorporated herein by this reference.

FIELD OF INVENTION

The present invention relates to a Siraitiae fructus product that is convenient for eating, and a method for preparing the same.

BACKGROUND OF INVENTION

Pharmacopoeia of the People's Republic of China (2010; p. 197) records that Siraitiae fructus is sweet in flavor and cool in property, and it belongs to the lung and large intestine meridians, it can reduce fever, moisturize the lungs, relieve sore throat and restore voice, and it also functions as a laxative. Siraitiae fructus is commonly used to treat cough caused by lung heat, sore throat, voice loss, and constipation. Modern research shows that Siraitiae fructus contains tetracyclic triterpenoid saponins, and especially, it has a high content of mogroside V. Therefore, Pharmacopoeia of the People's Republic of China requires that Siraitiae fructus be calculated as dry goods, and should contain no less than 0.50% of mogroside V. The sweetness of Siraitiae fructus is about 300 times of sucrose; it is not easily dissolved by the human digestive system and thus provides limited calories. Due to its safe and stable properties, Siraitiae fructus and its extracts are gradually becoming an ideal food for people having diabetes and obesity.

Because fresh Siraitiae fructus is difficult to store and transport, dried Siraitiae fructus has historically been consumed as both food and herb. However, three main concerns exist when people consume dried Siraitiae fructus: (1) it is difficult to control dosage. Siraitiae fructus has a high degree of sweetness, thus a low dosage would result in a not sweet enough taste, while a high dosage would affect the taste due to too much sweet. Furthermore, the sweetness in Siraitiae fructus varies a great deal due to factors such as breeds, origins, drying methods, harvesting time, etc. Therefore, both the inexperienced and the experienced technicians need to perform preliminary experiments to determine the proper dosage for each batch of Siraitiae fructus; (2) it is difficult to maintain the taste. Fresh Siraitiae fructus is a fragrant and genuinely sweet fruit. Because it has a dense and tight fruit peel, roasting under high-temperature for a longtime is required to obtain dried Siraitiae fructus. However, even dried Siraitiae fructus processed with high-level roasting techniques still has a strong sweet flavor and some degree of burnt odor, due to the drying process. Moreover, most dried Siraitiae fructus products are processed by fruit farmers in their simple and crude ovens; the flesh usually is roasted to dark brown color, and has a distinct burnt taste and a bitter flavor. Dried Siraitiae fructus made from dead Siraitiae fructus or unripe Siraitiae fructus fruit would have an even worse taste; (3) it is difficult for consumers to determine whether to accept or to discard the fruit peel. The Siraitiae fructus fruit peel itself does not have an obvious sweetness. However, through the drying process under high temperature, part of the flesh liquefied and passed to the peel through capillary action or dripping on the peel, resulting that the peel has a markedly sweet taste. This confuses consumers in that they are not certain whether the peel can be consumed or not. It would be a waste to discard the peel because it is sweet regardless; however, some consumers cannot accept the peel because it is dark and fluffy, and seems dirty. Due to the above concerns, it often happens that consumers would steep a half or full dried Siraitiae fructus fruit in several hundred milliliters of water. The taste is acceptable at the beginning; as the amount of water reduces, however, the amount of dissolved Siraitiae fructus increases. This causes the Siraitiae fructus solution to have a stronger degree of sweet taste, burnt odor, and bitter flavor, and also gives the solution a darker color, and resulted in the eventual discard of the Siraitiae fructus solution.

With the gradual familiarization and recognition of its function as a dietary supplement, as well as the advance in food and drug processing techniques, products containing Siraitiae fructus as the main ingredient are emerging. Until now, 137 invention patents relating to Siraitiae fructus can be found in the patent information database of the State Intellectual Property Office of the People's Republic of China. Of those, 55 patents relate to food or dietary supplement products, including: 14 patents directed at fruit wine or fruit vinegar containing Siraitiae fructus and other ingredients; 8 patents relate to solid products containing original plants, exemplified by tea, that are made from Siraitiae fructus and other ingredients; 12 patents relate to dissolvable solid food or low-calorie sweetener that contains Siraitiae fructus and other ingredients; and 7 patents relate to products comprising Siraitiae fructus as the only ingredient.

Of all the edible materials, not many drinks made from one single ingredient are good in color, smell, and taste; Siraitiae fructus is one of the few. Obviously, it would damage the characteristics of Siraitiae fructus if it is used as a common ingredient together with other materials in a formula to produce an end product.

In one of the 7 patents that relate to products containing only Siraitiae fructus, i.e., patent application number 200610021160.X, titled "Siraitiae fructus product and method for preparing same", relates to a drying process where Siraitiae fructus flesh is pulp and then coated on a roasting device for drying; patent application number 200510020314.9, titled "fresh Siraitiae fructus powder and preparation method thereof", relates to a process where fresh Siraitiae fructus is freeze dried and pulverized; patent application 200810174726.1, titled "method for preparing fresh Siraitiae fructus freeze-dried superfine powder", relates to a process where pre-frozen, pulverized Siraitiae fructus is vacuum dried at a temperature of between 40° C. and 120° C., and then super-fined; patent application number 200910114443.2, titled "Fructus momordicae instant powder and preparation method thereof", relates to treating Siraitiae fructus extract with several enzymes before drying; patent application number 200810001670.X, titled "Siraitiae fructus sweetener and preparation method", relates to extracting dry powder from whole Siraitiae fructus and mixing the same with mogroside at different ratios; patent application number 200510066542.X, titled "Preparation method for Siraitiae fructus juice", relates to filtering, press filtering, micro-filtering, and nano-filtering Siraitiae fructus juice to produce liquid drinks; patent application number 200810097509.7, titled "De-colored Siraitiae fructus juice and method for preparing the same", relates to de-coloring Siraitiae fructus juice with resin, and then acidifying it to produce a white or yellowish transparent liquid.

Compared with other compound products, these seven patented products have advantages in keeping and displaying the characteristics of Siraitiae fructus, and improving the homogeneity of product quality. However, they still have obvious drawbacks: (1) the last two patented products are liquid preparations; complex processing techniques are required; and preservatives are added to conserve the products; (2) the fourth and fifth patented products have a high degree of sweetness and are inconvenient to use. Dry powder made from Siraitiae fructus water is about 20 times sweeter than sucrose. A further fine preparation causes dry powder to have a mogroside V content of 30%, and that is about 100 times sweeter than sucrose. Suppose a consumer prepares a 200 ml drink, only 15 g of sucrose would be needed to achieve an ideal degree of sweetness. However, if Siraitiae fructus extract is used as the sweetener, then only 0.75 g of Siraitiae fructus extract powder is needed, and only 0.15 g of crude saponin powder is needed. Such a small amount is inconvenient for packaging and usage; (3) the first three patented products are obtained from directly pulverizing fresh Siraitiae fructus, and then drying. Although properties such the degree of sweetness and the ability to absorb moisture of these products are not as good as those of the fourth and fifth patented products, they are feasible in terms of packaging and determining quantity. However, there still exist three disadvantages: (1) in these products, the non-edible Siraitiae fructus peel and seeds are pulverized together with flesh and end up being ingested by consumers. The impure contents from the peel render a high level of microorganisms in the final products, and the fatty acids from the seeds render the products an unpleasant odor and make the final products susceptible to rancidity; (2) when dried under low-temperature conditions, Siraitiae fructus enzyme activities are well-kept, thus rendering the final product a numbing feeling; and (3) whole fruit powder products have a lot of suspended and precipitated substances, rendering the liquid solution an unaesthetic appearance.

SUMMARY OF THE INVENTION

Aim of the invention is to provide a Siraitiae fructus product that is convenient for eating, has a unique flavor, and has a high content of mogroside V.

This invention also aims at providing a preparation method of such a Siraitiae fructus product, wherein the method is efficient and the product prepared by this method has the advantage of fine stability.

This invention also aims at providing another preparation method, wherein the method is energy efficient and saves resources, and the investment in the preparation facilities is low.

This invention provides a Siraitiae fructus product, characterized that it uses Siraitiae fructus seeds as carriers, and Siraitiae fructus flesh is coated on the seeds.

This invention further provides a Siraitiae fructus product, wherein the carriers are coated with Siraitiae fructus flesh and other formula ingredients.

This invention further provides a Siraitiae fructus product, when calculated by the dry weight of flesh and seeds, contains no less than 0.5% of mogroside V; preferably, contains no less than 1% of mogroside V; more preferably, contains no less than 1.5% of mogroside V.

The flesh can be the original flesh tissue, or flesh pulp prepared by physical methods; other formula ingredients include adjuvant substances and/or functional substances (substances having supplemental or treatment functions); adjuvants include food additives such as acids, for example, citric acid, flavoring essences, preservatives, baking soda, calcined soda, honey, and vitamins, etc.; functional substances include extract of any of the following or a combination of a few of the following Chinese medicine: star aniseed (Anisi Stellati Fructus), common fennel (Foeniculi Fructus), clove (Caryophylli Flos), ginger (Zingiberis Rhizome), cinnamon (Cinnamomi Cortex), dried orange peel (Citri Reticulatae Pericaium), chrysanthemum (Chrysanthemi Flos), wild chrysanthemum (Chrysanthemi Indici Flos), honeysuckle (Lonicerae Japonicae Flos), mint (Menthae Haplocalycis Herba), lotus leaf (Nelumbinis Folium), reed root (Reed Rhizome), Alpiniae Oxyphyllae Fructus, Lophatheri Herba, Phyllanthi Fructus, liquorice (Glycyrrhizae Radix), malt (Hordei Fructus Germinatus), Hovenia dulcis Thunb, Gardenia Fructus, Cassiae Semen, Amomi Fructus, Citri Exocarpium Rubrum, Platycodonis Radix, Perillae fructus, Imperatae Rhizoma, corn stigma, Mume Fructus, dates (Jujubae Fructus), Dioscoreae Rhizoma, papaya (Chaenomelis Fructus), hawthorn (Crataegi Fructus), Puerariae Lobatae Radix, flower of lobed Kudzuvine, Flos Sophorae Immaturus, Mod Cortex, Mori Ramulus, Mori Folium, Mori Fructus, chicory (Cichorii Herba), wolfberry (Lycii Fructus), almond (Armeniacae Semen Amarum), Astragali radix, Codonopsis Radix, ginseng (Ginseng Radix et Rhizoma), Notoginseng radix et Rhizoma, salvia miltiorrhizae radix et Rhizoma, rhubarb (Rhei Radix et Rhizoma), Polygoni multiflori radix, aloe, Morindae Officinalis Radix, poria, Rhodiola Crenulatae Radix et Rhizoma, Rehmanniae Radix, Stercculliae Lychnophorae Semen, Glehniae Radix, Eriobotryae Folium, Ophiopogonis Radix, Ligustri Lucidi Fructus, magnoliae officinalis cortex, Cyperi Rhizoma, Leonuri Herba, Centellae Herba, Ginkgo Folium, leaf of Chinese holly, Eucommiae Cortex, Rosae Laevigatae Fructus, Arctii Fructus, Cordyceps, tea, etc.

Method 1: this invention provides a method for preparing a Siraitiae fructus product; the method includes the following steps:

Step 1: removing Siraitiae fructus peel;
Step 2: separating Siraitiae fructus flesh and seeds;
Step 3: drying the seeds;
Step 4: preparing flesh pulp; and
Step 5: coating the flesh pulp on the surface of the dried seeds.

In step 1, the Siraitiae fructus peel removal rate is no less than 50.0%; preferably, the removal rate is no less than 90.0%; more preferably, the removal rate is no less than 98.0%. The sweet flesh part that is adhered on the inside of the Siraitiae fructus peel is preferably recovered through manual or mechanical methods, and is then added into the flesh pulp according to step 4 for further utilization.

In step 2, the purpose of separating the flesh and seeds is to get the flesh that is adhered on the surface of the seeds, and then to collect and store the flesh separately; after separation, the seeds are in a dispersed state, and preferably the seeds are in a state that they are separated from each other; both manual and mechanical methods can be applied to separate the flesh and seeds; preferably, separation machines are used to separate seeds and flesh.

The separated seeds from step 3, containing about 50% of water, are dried separately for the purpose as follows: (1) the flesh exerts a lot of resistance for removing the water contained in the seeds; after separating the flesh from the seeds, speed of drying the seeds becomes relatively last; (2) the procedure of drying reduces the weight ratio of flesh, thus the attached seeds are easily separated through physical methods; and (3) dried seeds have better mobility and are light in weight, thus are easily turned in the boiling bed, and such seeds have a relatively higher carrying capacity of flesh pulp. Seeds can be dried directly, or can be treated first to reduce the amount of flesh before drying, such as centrifuging, rinsing in cold water, soaking in hot water, etc. The centrifuge solution or the water treatment solution contains a certain amount of Siraitiae fructus content, and it is preferably to recover the solution for further utilization. Seeds drying methods include one or a combination of a few of the following: drying in the shade, drying under the sun, roasting, microwave drying, infrared light drying, vacuum drying, and freeze drying; preferably, seeds are dried using one or a combination of a few of the following: drying in the shade, drying under the sun, roasting, vacuum drying, and microwave drying; the range of the drying temperature is between 20° C. and 120° C.; preferably, the temperature is maintained at between 40° C. and 100° C.; more preferably, it is at between 60° C. and 80° C.; the content of water in the seeds after drying should be within 50%; preferably, it is maintained within 20%; more preferably, it is within 10%.

The flesh pulp in step 4 can be prepared by grinding the flesh into pulp, or be prepared using pulping machines that are available on the market, such as soymilk machine, ball mill, etc.; the fineness of the flesh pulp is maintained at between 10 and 300 fineness units, and preferably at between 50 and 200 fineness units, and more preferably at between 60 and 120 fineness units.

Adjuvant and/or functional substances (substances having supplemental or treatment functions) can be added into the flesh pulp in step 4; adjuvants include food additives such as acids, for example, citric acid, flavoring essences; preservatives, baking soda, calcined soda, honey, and vitamins, etc.; functional substances include extract of any of the following or a combination of a few of the following: star aniseed (Anisi Stellati Fructus), common fennel (Foeniculi Fructus), clove (Caryophylli Flos), ginger (Zingiberis Rhizome), cinnamon (Cinnamomi Cortex), dried orange peel (Citri Reticulatae Pericarpium), chrysanthemum (Chrysanthemi Flos), wild chrysanthemum (Chrysanthemi Indici Flos), honeysuckle (Lonicerae Japonicae Flos), mint (Menthae Haplocalycis Herba), lotus leaf (Nelumbinis Folium), reed root (Reed Rhizome), Alpiniae Oxyphyllae Fructus, Lophatheri Herba, Phyllanthi Fructus, liquorice (Glycyrrhizae Radix), malt (Hordei Fructus Germinatus), Hovenia dulcis Thunb, Gardenia Fructus, Cassiae Semen, Amomi Fructus, Citri Exocarpium Rubrum, Platycodonis Radix, Perillae fructus, Imperatae Rhizoma, corn stigma, Mume Fructus, dates (Jujubae Fructus), Dioscoreae Rhizoma, papaya (Chaenomelis Fructus), hawthorn (Crataegi Fructus), Puerariae Lobatae Radix, flower of lobed Kudzuvine, Flos Sophorac Immaturus, Mori Cortex, Mod Ramulus, Mori Folium, Mori Fructus, chicory (Cichorii Herba), wolfberry (Lycii Fructus), almond (Armeniacae Semen Amarum), Astragali radix, Codonopsis Radix, ginseng (Ginseng Radix et Rhizoma), Notoginseng radix et Rhizoma, salvia miltiorrhizae radix et Rhizoma, rhubarb (Rhei Radix et Rhizoma), Polygoni multiflori radix, aloe, Morindae Officinalis Radix, poria, Rhodiola Crenulatae Radix et Rhizoma, Rehmanniae Radix, Sterculliae Lychnophorae Semen, Glehniae Radix, Eriobotryae Folium, Ophiopogonis Radix, Ligustri Lucidi Fructus, magnoliae officinalis cortex, Cyperi Rhizoma, Leonuri Herba, Centellae Herba, Ginkgo Folium, leaf of Chinese holly, Eucommiae Cortex, Rosae Laevigatae Fructus, Arctii Fructus, Cordyceps, tea, etc. After mixing the adjuvant and/or functional substances with the flesh pulp, the mixture is coated on the surface of the seeds for drying; preferably, extracts containing flavoring essences or volatile ingredients are spray-coated after the seeds and flesh pulp are dried, and then mixed with the flesh pulp or dried with the flesh pulp under low temperature.

According to the concentration, the flesh pulp of step 4 can be concentrated or diluted with water before applying step 5.

In step 5, after coating the flesh pulp on the dried seeds surface, a further drying step is preferred. The dried product contains no more than 30.0% of water; preferably, contains no more than 20.0% of water; more preferably, no more than 10.0% of water. In the drying process, seeds are put into the drying facility first, then flesh pulp is added while heating; drying facilities include sugar coating pan, high performance coating pan, one-step granulator, boiling drying bed, and other similar machinery.

Said method for preparing a Siraitiae fructus product can include an additional packaging step, such as directly packing the flesh coated dried seeds into bottles or bags, or packing the final products in tea bags first, and then packing the tea bags into other packaging equipment.

Method 2: this invention provides another method of preparing a Siraitiae fructus product, wherein a majority of the flesh is naturally condensed and tightly pressed on the surface of the seeds after drying. The method includes the following steps:

Step 1: obtaining Siraitiae fructus flesh masses by peeling, and then drying;

Step 2: increasing surface area of flesh masses through physical methods, and then drying;

Step 3: separating the tightly attached seeds through physical methods, and then drying.

In step 1, the removal rate of the peel is no less than 50.0%; preferably, the removal rate is no less than 90.0%; more preferably, the removal rate is no less than 98.0%. The flesh mass is the Siraitiae fructus without the peel, a sphere-shaped object consisting of the flesh and seeds.

In step 2, the physical methods to increase the surface area of the flesh mass include manually or mechanically breaking open, cutting open, or press flattening the flesh mass. By increasing the surface area of the flesh and seeds, the drying speed is increased. The flesh mass can be randomly broken open, cut open, or split by force; preferably, the flesh mass containing the seeds is split lengthways along the Siraitiae fructus; more preferably, with the method of splitting the flesh mass lengthways the seeds of the Siraitiae fructus separate by rows with the connection of the flesh and the sphere-shaped flesh mass is turned into a tile shape (see FIG. 3). The surface area of the flesh mass after step 2 would be about 120% of the original flesh mass surface area; preferably, The surface area of the flesh mass after step 2 is about 150% of the original surface area; more preferably, The surface area of the flesh mass after step 2 is about 200% of the original surface area.

In step 3, the seeds separated through physical methods become single particles, or several seeds are connected via flesh but in an easily break open for eating status; the physical separation methods include manually or mechanically breaking open, cutting out, or slicing, etc.

The drying methods in steps 1 to 3 include one or a combination of a few of the following methods; drying in the shade, drying under the sun, roasting, microwave drying, infrared light drying, vacuum drying, and freeze drying; preferably, the drying methods include one or a combination of a few of the following: drying in the shade, drying under the sun, roasting, vacuum drying, and freeze drying.

The purpose of the drying in step 1 is to remove part of the water, and further to reduce the mobility of the flesh, weaken the adhesion of flesh to the drying facility and decrease the attrition of the flesh in the process of increasing surface area of flesh mass in step 2. The water removal rate of this step is between 5% and 90%; preferably, the removal rate is between 10% and 80%; more preferably, the removal rate is between 10% and 60%; even more preferably, it is between 10% and 30%.

The drying process in step 2 is the fast drying step after the increase of the flesh mass surface area. After drying in this step, the remaining water renders the flesh some flexibility for further separation of the seeds, and it also prevents the separated seeds from attaching to each other again. The water removal rate of this step is between 5% and 90%; preferably, it is between 20% and 80%; more preferably, the rate is between 40% and 70%.

The drying step in step 3 is the process to remove water after the final product molded. The aim is to improve the convenience for consuming the product and to increase the quality of the product. This step separates the tightly attached seeds; it further increases the surface area of the flesh mass and accelerates the drying speed, and it also renders the final product more convenient for eating. The water content after drying of this step is no more than 30.0%; preferably, no more than 15.0%; more preferably, no more than 10.0%.

The drying temperature in steps 1 to 3 is between 20° C. and 120° C.; preferably, between 40° C. and 100° C.; more preferably, between 60° C. and 80° C.

The relative humidity of the drying process is maintained at between 2% and 40%.

Preferably, the relative humidity is maintained at between 5% and 30%;

More preferably, the relative humidity is maintained at between 6% and 20%;

More preferably, the relative humidity is maintained at between 8% and 18%.

The method for maintaining the relative humidity of the Siraitiae fructus drying process at between 5% and 30% includes the step of replacing the humid air surrounding the Siraitiae fructus with a one-way flowing airflow having a humidity of between 5% and 30%; preferably, this is achieved through a dehumidifying device; more preferably, Siraitiae fructus is put within an air-tight drying unit, wherein the air-tight drying unit includes an air input port and an air output port that are connected with an air output port and an air input port on the dehumidifying device, respectively; the dehumidifying device imports air into the air-tight drying unit, wherein the air has a humidity of between 5% and 30% and a temperature of between 30° C. and 80° C.; the dehumidifying device also exports the air inside the air-tight drying unit into the dehumidifying device, thus the air circulates between the dehumidifying device and the air-tight drying unit to maintain the humidity of the air-tight, dry unit of between and 30%. The dehumidifying device can be purchased on the market, or used as is known in the art, for example, as described in patent application CN200910007224.4

After steps 1 to 3, the final products can be directly packaged in to bottles or packs and ready for sale. All kinds of essential oils or substance extracts can be sprayed on the products, and after mixing or dry-processing, the products can be packaged with packing equipments. Substance extracts that can be sprayed on the products include: star aniseed (Anisi Stellati Fructus), common fennel (Foeniculi Fructus), clove (Caryophylli Flos), ginger (Zingiberis Rhizome), cinnamon (Cinnamomi Cortex), dried orange peel (Citri Reticulatae Pericarpium), chrysanthemum (Chrysanthemi Flos), wild chrysanthemum (Chrysanthemi Indici Flos), honeysuckle (Lonicerae Japonicae Flos), mint (Menthae Haplocalycis Herha), lotus leaf (Nelumbinis Folium), reed root (Reed Rhizome), Alpiniae Oxyphyllae Fructus, Lophatheri Herba, Phyllanthi Fructus, liquorice (Glycyrrhizae Radix), malt (Hordei Fructus Germinatus), Hovenia dulcis Thunb, Gardenia Fructus, Cassiae Semen, Amomi Fructus, Citri Exocarpium Rubrum, Platycodonis Radix, Perillae fructus, Imperatae Rhizoma, corn stigma, Mume Fructus, dates (Jujubae Fructus), Dioscoreae Rhizoma, papaya (Chaenomelis Fructus), hawthorn (Crataegi Fructus), Puerariae Lobatae Radix, flower of lobed Kudzuvine, Flos Sophorac Immaturus, Mori Cortex, Mori Ramulus, Mori Folium, Mori Fructus, chicory (Cichorii Herba), wolfberry (Lycii Fructus), almond (Armeniacae Semen Amarum), Astragali radix, Codonopsis Radix, ginseng (Ginseng Radix et Rhizoma), Notoginseng radix et Rhizoma, salvia miltiorrhizae radix et Rhizoma, rhubarb (Rhei Radix et Rhizoma), Polygoni multiflora radix, aloe, Morindae Officinalis Radix, poria, Rhodiola Crenulatae Radix et Rhizoma, Rehmanniae Radix, Sterculliae Lychnophorae Semen, Glehniae Radix, Eriobotryae Folium, Ophiopogonis Radix, Ligustri Lucidi Fructus, magnoliae officinalis cortex, Cyperi Rhizoma, Leonuri Herba, Centellae Herba, Ginkgo Folium, leaf of Chinese holly, Eucommiae Cortex, Rosae Laevigatae Fructus, Arctii Fructus, Cordyceps, tea, etc.

The preparation method as described in Method 2 can be simplified as follows:

Simplified Method 1:

Step 1: removing fresh Siraitiae fructus peel to obtain Siraitiae fructus flesh masses, increasing flesh masses surface area through physical methods, and then drying;

Step 2: separating seeds through physical methods to turn the tightly attached seeds into rows of seeds, wherein each row contains 1 to 10 seed particles, and then drying.

Simplified Method 2:

Step 1: removing fresh Siraitiae fructus peel to obtain flesh masses, and then drying;

Step 2: increasing flesh masses surface area through physical methods, and separating tightly attached seeds through physical methods, and then drying.

Simplified Method 3:

Removing fresh Siraitiae fructus peel to obtain flesh masses, increasing flesh masses surface area through physical methods, and then drying.

Simplified Method 4:

Removing fresh Siraitiae fructus peel to obtain flesh masses, and then drying.

The above four simplified preparation methods can achieve similar or partial final product effects. However, simplified method 1 can cause extra flesh to stick on the drying facility, or can cause extra flesh to be separated from seeds, thus it is low in energy consumption but high in material consumption; as for simplified method 2, in order to avoid re-attachment of the separated seeds, drying process is performed when the flesh masses surface area is relative small and for a longer period of time, thus it is relatively high in energy consumption; simplified method 3 is a one-step process; it is simple to operate, but has several disadvantages: (1) extra flesh is stuck on the drying facility during drying; and (2) after drying, there are chunks of product attached together, thus extra powder occurs in the later packaging and consuming stages. These issues cause a high waste in materials; simplified method 4 is also a one-step process; material consumption is low during the drying process, but energy consumption is high, and during consumption, the product is hard to break open and has extra powder, causing a waste.

Therefore, the three-step drying process according to this invention is the preferred preparation method, considering factors such as energy consumption, material consumption, and characteristics of final product.

The product according to this invention has the following advantages:

1. It is pure and sanitary. Removal of the Siraitiae fructus peel efficiently avoids the undesired effects caused by the unhealthy substances on the peel, such as the fluff, microorganisms, wax, dust, and etc., and it also helps to reduce the level of pesticide residue of the final product.

2. It has a genuine and original taste. After roasting at a temperature between 50° C. and 100° C., the raw stinky odor of fresh Siraitiae fructus is removed, rendering the final product a rich fragrant smell, the flesh and seeds a bright yellowish color, and an authentic flavor; besides the product has the advantage of fine stability, 3. It is convenient to use and has a high degree of sweetness. This product with the seeds as carriers and each Siraitiae fructus seed can be diluted to make a 50 ml, light-yellow solution; it has a degree of sweetness of about 2-4 times more than a common dry Siraitiae fructus product of the same weight. Because this product is easy to adjust dosage, it is easy to find an ideal dosage according to the varying tastes of consumers and different volume of containers.

The preparation method according to the invention has the following advantages:

1. It is low in energy consumption. In this invention, the Siraitiae fructus peel is removed first, then broken open to dry, thus the drying speed is substantially increased and the energy consumption is markedly reduced. This invention provides a preparation method, this is, separating the seeds and flesh first, thus the seeds are rapidly dried, and then the seeds are coated with the flesh pulp to make the final product. Because of the increased surface area, drying speed is fast and has an energy consumption lowering effect.

2. It is convenient to manufacture. The drying method provided in this invention, i.e., drying the broken-open flesh and seeds, is applicable to manual production, is low in facility investment cost, and it provides a lot of employment opportunities; the preparation design according to this invention, i.e., separating the flesh and seeds first, then drying, is not a complex technical process, thus is applicable to industrial production, and has a steady product quality, and is convenient for automatic packaging.

3. Raw material purchase is convenient. Fresh Siraitiae fructus and dried Siraitiae fructus are both sold according to their sizes as extra large, large, medium, small, and extra small. Fresh Siraitiae fructus of different specifications require different length of drying. The drying speed according to the claimed invention, however, is relatively identical, and has no limitations on the Siraitiae fructus specifications.

4. Content of the effective ingredient is high. Mogroside V is the main sweet ingredient of Siraitiae fructus; it is also the major potent substance of Siraitiae fructus. The preparation method according to the claimed invention reduces the flesh attrition rate during processing to the maximum extent; also, the quick drying of Siraitiae fructus greatly reduces mogroside V attrition during the heating process. Thus, a product according to the claimed invention contains more than 1.0% of mogroside V, which is two times higher than the standard required by the Pharmacopoeia.

Therefore, because of the advantages in product quality, low energy consumption, convenience for eating, etc., this invention will greatly promote the development and advancement of the Siraitiae fructus product industry.

DETAILED DESCRIPTION OF THE EMBODIMENTS

Figure 1:
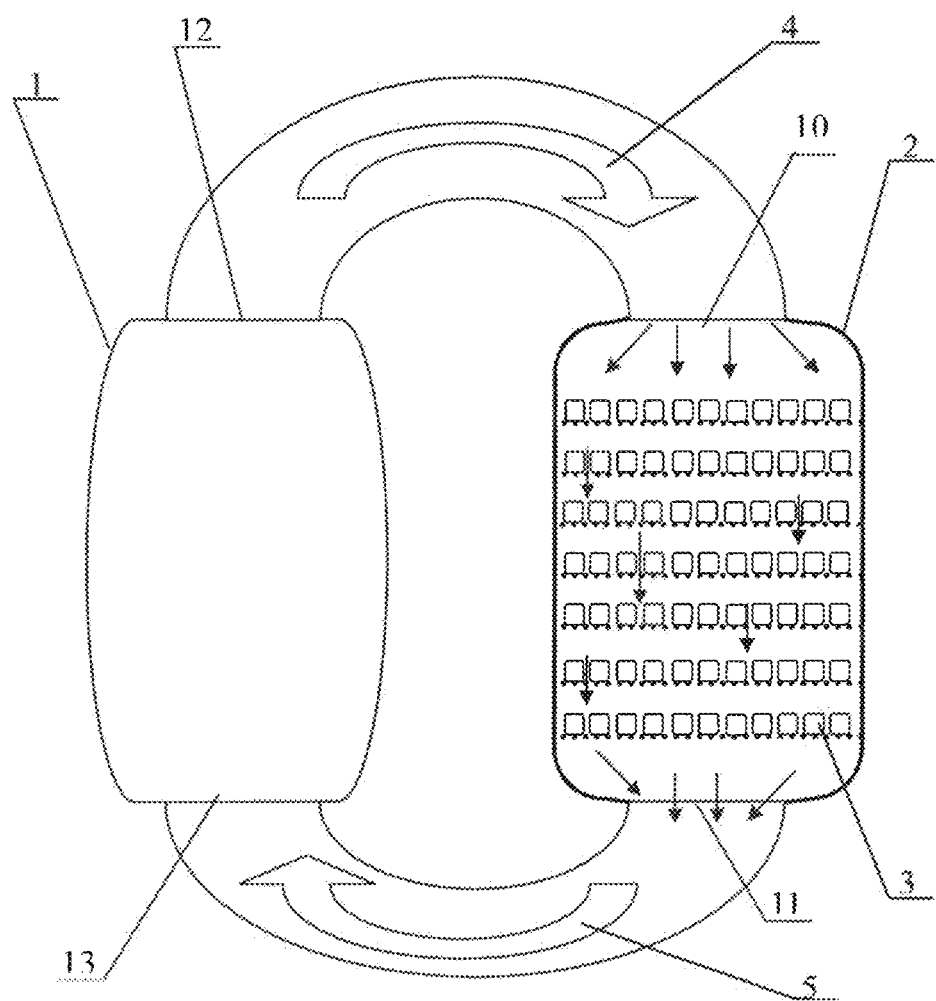
FIG. 1. Schematic of a dehumidifying drying device
Dehumidifying drying device according to FIG. 1 includes dehumidifying device (1), drying cabinet (2), Siraitiae fructus (3), an air flow with relatively low humidity and a relatively high temperature (4), an air flow of relatively high humidity and a low temperature air flow (5), an input port of the drying cabinet(10), an output port of the drying cabinet(11), an output port of the dehumidifying device(12), an intput port of the dehumidifying device(13).
Figure 2:
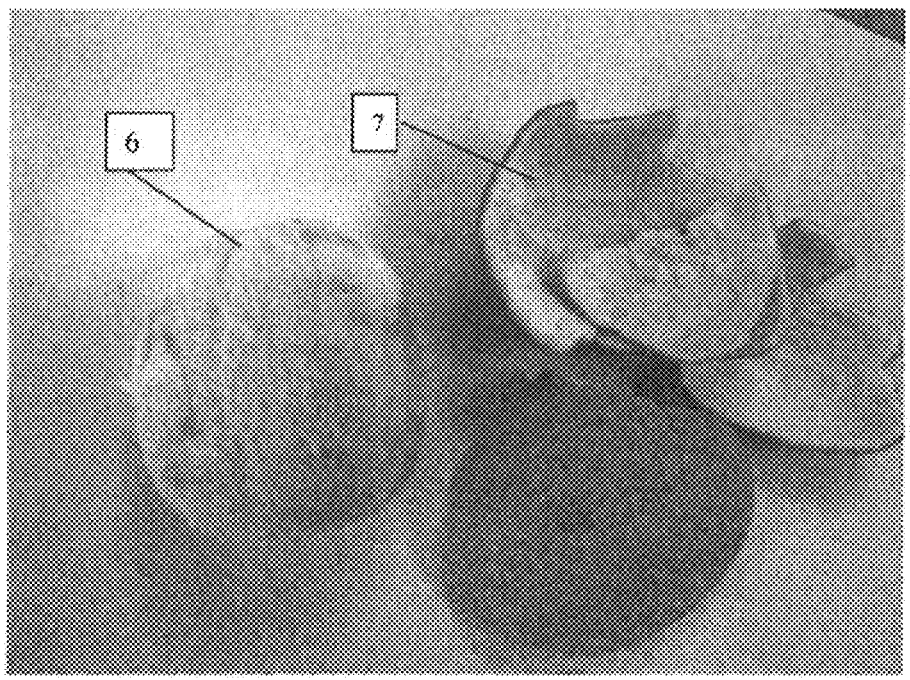
FIG. 2. Flesh mass (6) including flesh and seeds, and peel (7).
Figure 3:
FIG. 3. Schematic of flesh and seeds after broken-open.

The invention is further illustrated by the following examples:

EXPERIMENT 1

15 large-sized fresh Siraitiae fructus were obtained, 5 of which were in the control group, and the rest 10 Siraitiae fructus were removed the peel. Then put all of the 15 Siraitiae fructus in a constant-temperature oven, and adjusted the temperature at 60° C. Siraitiae fructus was taken out of the oven at different times, and their weights were accurately measure, and the rates of weight loss were calculated (5 of the peel-removed flesh masses were broken open after heating for 60 minutes, and were then dried continuously). The results were shown in Table 1.

TABLE 1

The percentage* of weight loss of *Siraitiae* fructus according to different treatments at 60° C.

| | Length of drying | | | | | | | |
|---|---|---|---|---|---|---|---|---|
| | 30 min | 60 min | 90 min | 120 min | 180 min | 250 min | 300 min | 360 min |
| Fresh *Siraitiae* fructus | 0.19 | 0.43 | 0.76 | 1.08 | 1.83 | 2.54 | 3.12 | 3.91 |
| Flesh mass | 6.34 | 12.14 | 16.86 | 20.09 | 25.83 | 30.20 | 32.63 | 35.30 |
| Broken open flesh mass | 5.01 | 10.56 | 21.72 | 29.15 | 38.36 | 47.58 | 51.92 | 56.01 |

*Percentage of weight loss = (original weight − weight after drying)/original weight × 100

The results show that, relative to fresh Siraitiae fructus, drying speed of flesh mass after removing the peel was about 10 times faster; relative to non-treated flesh mass, breaking open flesh mass increased the drying speed by about one time. If the flesh mass was directly dried to the water content at which the final product can be preserved for long time (the content of water was no more than 15%), the final product would form a hard mass and would be hard to break open by hand or slice open with a knife; it would also cause the spilling of extra power, resulted in inconvenience for eating.

EXPERIMENT 2

10 fresh Siraitiae fructus were peeled to obtain flesh mass and then dried at 50° C. When the weight loss was at about 15%, all the flesh masses were broken open and continued to dry. When the weight loss was at about 20%, the flesh masses were taken out and randomly divided into two groups, and each group contained 5 flesh masses. The weights of the two groups were measured. For one of the groups, the tightly attached seeds were separated from each other, while the other group was used as the control group. Both groups were dried at 50° C., and taken out at a specified time. Their weights were measured, and the rates of weight loss were calculated. The results were shown in Table 2.

TABLE 2

Effect of separating the tightly attached seeds on the rate of weight loss* at drying at 50° C.

| | Length of drying | | | | |
|---|---|---|---|---|---|
| | 20 min | 40 min | 60 min | 90 min | 120 min |
| Attached seeds were separated | 10.05 | 16.13 | 19.76 | 23.06 | 25.78 |
| Attached seed were not separated | 6.34 | 10.87 | 14.37 | 17.37 | 20.36 |

*Percentage of weight loss = (original weight − weight after drying)/original weight × 100

Data in Table 2 show that separating the tightly attached seeds markedly improved the drying speed of Siraitiae fructus. This was also related to the increased surface area of the drying material. Therefore, when the broken open flesh masses are dried to a certain extent, it is then suitable to separate the tightly attached seeds, in order to reduce energy consumption and to improve the convenience for eating.

EXPERIMENT 3

20 Siraitiae fructus were peeled to obtain flesh masses. Flesh masses were randomly divided into two groups, each containing 10 flesh masses. Flesh masses in the first group were put in sieve and dried at 60° C. When the water was removed at about 20%, the flesh masses were broken open and continued to dry at 60° C. to remove about 40% of water; then the tightly attached seeds were separated and continued to dry at 60° C. to remove 30% of water; then the flesh masses were taken out, product weight was measured; the dried flesh that stuck on the sieve was collected as flesh crumb, and the flesh crumb weight was measured. The flesh masses in the second group were pressed into flat sheets and put into another sieve, and dried at 60° C. When the water was removed at about 60%, the tightly attached seeds were separated, and continued to dry at 60° C. to remove 30% of water, and then the flesh masses were taken out and the product weight was measured; the dried flesh stuck on the sieve was also collected as flesh crumb and the flesh crumb weight was measured. Results were shown in Table 3.

TABLE 3

Comparison of Siraitiae fructus flesh weight loss from two processing methods

| | Group | |
|---|---|---|
| | 1 | 2 |
| Processing methods | Three steps drying method | Two steps drying method |
| Product weight | 185.6 g | 184.3 g |
| Flesh crumb weight | 0.297 g | 6.764 g |
| Percentage of weight loss* | 0.16% | 3.67% |

*Percentage of weight loss = flesh crumb weight/product weight × 100%

Above experiment data show that for peeled Siraitiae fructus, if the flesh mass was instantly broken open to dry, the ratio of flesh stuck on drying facility was much higher than the flesh mass which was properly dried first before broken open, as in the control group. Therefore, after removing the Siraitiae fructus peel, it is preferable that the flesh mass is dried to remove partial water first, then to increase its surface area for continuous drying.

EXPERIMENT 4

150 Siraitiae fructus were obtained and randomly divided into 3 groups; each group contained 50 Siraitiae fructus. Siraitiae fructus in Group 1 were directly dried at 80° C., and then a sample was taken and powdered; sifting the powdered sample that can get through a 60-unit sieve, and then calculating the content of mogroside V. In group 2, Siraitiae fructus peel was removed, and the flesh masses were firstly dried at 60° C. to remove 20% of water; and then the flesh masses were broken open to continue to dry at 60° C. to remove 40% of water; then the tightly attached seeds were separated, and continued to dry at 60° C. to remove 30% of water; a sample was taken and powdered, and sifting the powdered sample that can get through a 60-unit sieve, and calculating the content of mogroside V. In group 3, the Siraitiae fructus peel was removed, and flesh masses were pressed into flat sheets, and then dried at 60° C. to remove 90% of water; the tightly attached seeds were separated, and a sample was taken and powdered; sifting the powdered sample that can through a 60-unit sieve, and calculating the content of mogroside V (see Pharmacopoeia of the People's Republic of China (2010; p. 197) for measurement method of mogroside V). Results were shown in Table 4.

TABLE 4

Comparison of three processing methods Siraitiae fructus

| | Group | | |
|---|---|---|---|
| | Group 1 | Group 2 | Group 3 |
| Processing method | Traditional drying method | Three steps drying method | One steps drying method |
| Drying temperature | 80° C. | 60° C. | 60° C. |
| Length of process | 96 hrs | 8 hrs | 8 hrs |
| Appearance of the product | Peel was brown colored; flesh and seeds were chocolate brown colored | Golden; seeds had good integrity; flesh was relatively evenly coated on the surface of seeds | Golden; had more crushed seeds; coarse; flesh was not every evenly distributed |

TABLE 4-continued

Comparison of three processing methods *Siraitiae fructus*

|  | Group | | |
| --- | --- | --- | --- |
|  | Group 1 | Group 2 | Group 3 |
| Content of water | 9.5% | 10.3% | 9.5% |
| Content of mogroside V | 0.85% | 2.15% | 1.78% |

This experiment showed that when drying the products to contain about 10% of water, products from group 2 and 3 had obvious advantages in terms of appearance, content of effective ingredient, and energy consumption, as compared with products from group 1.

There are several comparisons to be made between group 2 and group 3. First, for the appearance, products from both groups had almost the same color; however, products from group 2 were more advantageous in terms of product integrity and even distribution of the flesh. Second, both processing methods in groups 2 and 3 were similar with regard to energy consumption; the flesh masses in group 3 were broken open earlier, while in group 2, the attached seeds were broken open then dried. Third, with regard to the length of processing, although there were three steps in group 2, the one step drying method used in group 3 resulted in difficulty in breaking open the flesh masses before packaging. Thus, these two processing methods were overall similar in labor cost. Lastly, with regard to the amount of mogroside V, the mogroside V content in the products from group 2 was about 20% higher than products from group 3. The significant differences were resulted from the flesh loss due to drying and packaging steps in group 3, as the flesh contains most of mogroside V in Siraitiae fructus.

Above controlled experiment shows that the preparation method of this invention greatly improved the quality of Siraitiae fructus product, and also vastly reduced energy consumption.

EXPERIMENT 5

50 kg of fresh Siraitiae fructus were removed the peel to get the flesh masses; the flesh and seeds of the flesh masses were separated using a separating machine. The seeds were divided into four groups with each group weighed 3 kg; the four groups of seeds were then dried to contain about 10% of water at 40° C., 60° C., 80° C., and 100° C., respectively. Results were shown in Table 5.

TABLE 5

Effect of drying temperature on *Siraitiae fructus* seeds

| Drying temperature | Length of drying | Water content | Characteristics of product |
| --- | --- | --- | --- |
| 40° C. | 12 h | 9.5% | Light yellowish; some raw stinky smell |
| 60° C. | 7 h | 8.8% | Yellow, crisp; a distinct fragrance |
| 80° C. | 4 h | 8.1% | Yellow; crisp; a prominent fragrance |
| 100° C. | 3 h | 9.5% | Dark yellowish; crisp; a certain extent of burnt smell |

Everything considered, it is preferable to dry Siraitiae fructus seeds at a temperature of between 60° C. and 80° C.

EXPERIMENT 6

Dried Siraitiae fructus seeds were obtained and divided into 3 groups with each group weighted 10 kg, and put them in a one-step granulator. The temperatures of input air were set at 60° C., 80° C., and 100° C., respectively. Proper amount of flesh pulp was sprayed on the surface of the seeds inside the granulator and dried. Results were shown in table 6.

TABLE 6

Effect of drying temperature on *Siraitiae fructus* seeds

| Drying temperature | Length of drying | Content of water | Characteristics of product |
| --- | --- | --- | --- |
| 60° C. | 8 h | 10.8% | Yellow; crisp; smooth surface; a fragrant smell |
| 80° C. | 5 h | 11.3% | Golden; crisp; smooth surface; a distinct fragrant smell |
| 100° C. | 4 h | 10.6% | Dark yellowish; crisp; coarse surface; a certain degree of burnt smell |

Everything considered, the preferred drying temperature for flesh pulp and seeds is 80° C.

EXPERIMENT 7

Fresh Siraitiae fructus were obtained and divided into 12 groups with each group contained 100 Siraitiae fructus. The effect of relative humidity on drying speed was observed at different temperatures. See table 7.

TABLE 7

Rate of weight loss* of fresh *Siraitiae fructus* after drying for 3 hrs at set temperature and humidity

|  | Relative humidity | | | |
| --- | --- | --- | --- | --- |
|  | 40% | 30% | 20% | 10% |
| 40° C. | 0.37% | 0.57% | 0.97% | 1.65% |
| 50° C. | 1.07% | 1.80% | 2.75% | 4.84% |
| 60° C. | 2.05% | 3.62% | 5.53% | 8.56% |

*Rate of weight loss = (weight of fresh *Siraitiae fructus* − weight after dried)/weight of fresh *Siraitiae fructus*

The results show that drying temperature and relative humidity have distinct effect on the drying speed of Siraitiae fructus

EXPERIMENT 8

The applicant further optimized the drying system, and designed a dehumidifying drying device as shown in FIG. 1, wherein the end gas from heat exchange with the material was used as the input air for the dehumidifying device. This device was applied to dry Siraitiae fructus flesh and seeds, and greatly reduced energy consumption. See table 8.

TABLE 8

Comparison of drying efficiencies utilizing dehumidifying drying device and common oven device

|  | Drying device | |
| --- | --- | --- |
|  | Air blowing thermostatic oven | Dehumidifying device |
| Operating power | 4 KVA | 4 KVA |
| Temperature | 60° C. | 60° C. |
| Length of drying | 36 h | 24 h |

TABLE 8-continued

Comparison of drying efficiencies utilizing dehumidifying drying device and common oven device

| | Drying device | |
|---|---|---|
| | Air blowing thermostatic oven | Dehumidifying device |
| Drying materials | Flesh masses and broken open flesh masses | Flesh masses and broken open flesh masses |
| Number of Siraitiae fructus | 3000 | 3000 |
| Electric power consumption | 144 kilowatt-hour | 96 kilowatt-hour |
| Number of dried Siraitiae fructus per kilowatt-hour | 20.8 | 31.3 |

Data from table 8 show that a 33% reduction in energy consumption was achieved when utilizing the dehumidifying device, as compared with common oven device.

Embodiments for Carrying out the Invention

The following embodiments are intended merely to better illustrate the claimed invention, and do not pose a limitation on the scope of the invention.

Embodiment 1. Mechanism and Operating Principle of a Dehumidifying Device

A dehumidifying drying device (1) is shown in FIG. 1. Drying cabinet (2) is an air-tight drying unit, which can be used as a container for drying materials. The drying cabinet has an input port(10) and an output port(11), connected to an output port(12) and an input port(13) of the dehumidifying device (1), respectively. Dehumidifying drying device (1) can be purchased from the market. First, dehumidifying dying device (1) was connected with a power outlet, relative humidity of the dehumidifying drying device was set at between 5% and 30%, and temperature was set at between 30° C. and 80° C. Dehumidifying drying device (1), through its air output port, carried into drying cabinet (2) an air flow of relatively low humidity and a relatively high temperature, and then replaced the air flow of drying cabinet (2), which was of relatively high humidity and a relatively low temperature; the air of drying cabinet (2) entered dehumidifying drying device 1 through its air output port, which was then dehumidified and heated in dehumidifying drying device 1; and then a new circle began.

Embodiment 2

3000 fresh Siraitiae fructus was peeled to obtain flesh masses; put the flesh masses into a dehumidifying drying device as shown in FIG. 1; turned on the dehumidifying drying device and set relative humidity at 10% and temperature at 60° C. An inflow of dry air of 60° C. and humidity of 10% constantly exchanged heat and humidity with the Siraitiae fructus inside the drying cabinet, and produced an end gas having a temperature of less than 60° C. and relative humidity higher than 10%; the end gas then entered into the dehumidifying drying device and was replenished with the heat generated from operating of the device, and became dry air having less water and had a temperature of 60° C. and relative humidity of 10%; the dry air was then continued to be used to dry Siraitiae fructus. After drying for 5 hours, the flesh masses were taken out and broken open, and continued to dry; after drying for another 10 hours, the materials were taken out, and the tightly attached seeds were separated and cut into single-row shaped materials, and continued to dry. After 9 hours of drying, the device was stopped and cooled to room temperature, and the materials were packaged. The end products were golden colored and contained less than 15.0% of water.

Embodiment 3

Figure 4:
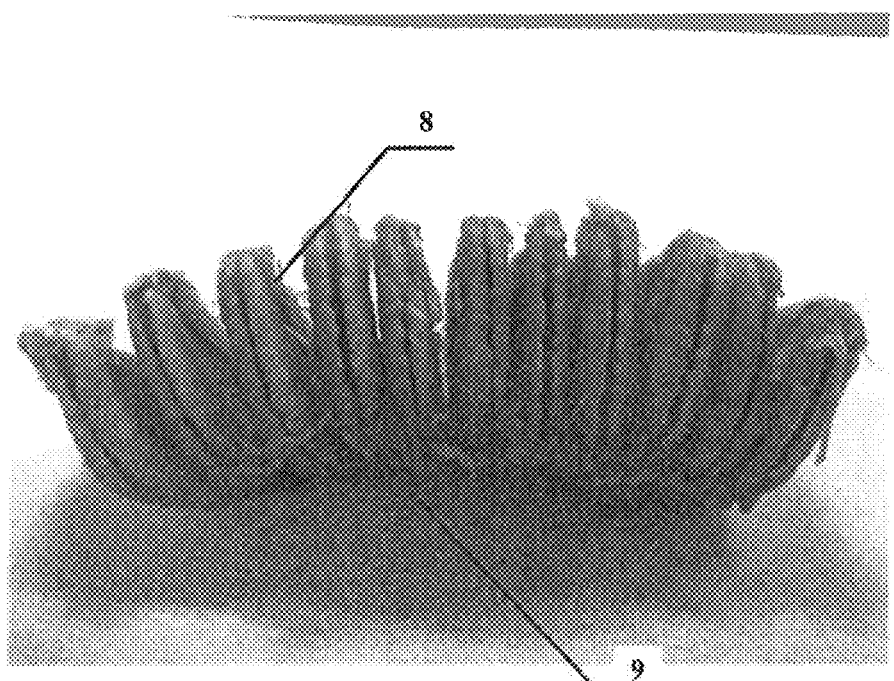
FIG. 4. Seeds (8) and dried flesh (9).
Figure 5:
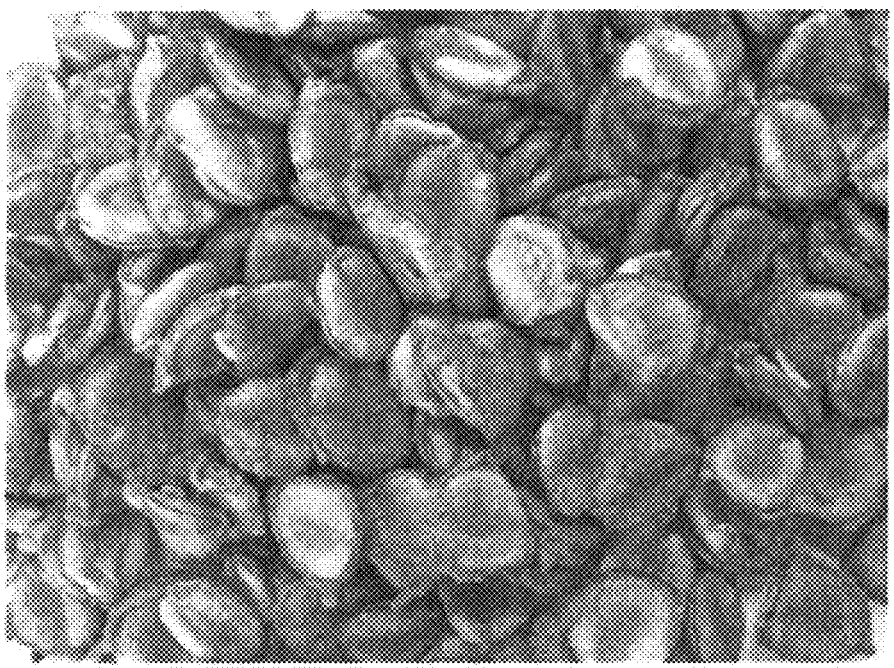
FIG. 5. Final product obtained after coating seeds surface with flesh pulp and then drying.

100 fresh Siraitiae fructus were peeled; put the flesh and seeds into an air blowing thermostatic oven to remove about 30% water at 50° C.; took out the materials and broke open the seed-containing flesh masses lengthways along the Siraitiae fructus to turn the flesh masses into tile-shape materials containing several rows of seeds; continued to dry the flesh masses at 50° C. to remove about 40% of water; took out and cut the tile-shape flesh masses lengthways into single rows, each containing 1 to 10 seeds; then using the flesh near the peel as the basis for connecting the seeds, separated the tightly attached seeds from the side opposite from the peel, and turned the product into a row of teeth-like material (see FIG. 4); continued to dry at 80° C. to reduce the content of water to less than 10.0%; took out the material, cooled to room temperature and packaged to obtain the final products.

Quality Standards of the Products:
(1) Properties: products were golden colored; contained one or several seeds; the flesh was brittle; tasted sweet and had the distinct Siraitiae fructus flavor;
(2) Water content: no more than 15.0%;
(3) Content of mogroside V: no less than 1.0% when calculated based on the dry product weight; and
(4) Directions and dosage: one seed per 50 ml hot water; ready to consume after steeping for 5 minutes.

Embodiment 4

10,000 fresh Siraitiae fructus were peeled and the seeds and flesh were separated using a separating machine; dried the seeds at 60° C. until water content was less than 10.0%; grinded the flesh with a grinding machine to obtain flesh pulp, and sifted the flesh pulp through a 80-unit silk sieve; put dried seeds into a coating pan, heated, and sprayed the flesh pulp on the dried seeds, and continued to dry until the water content was less than 10.0%; sifted and packaged the seeds to obtain the final products.

Quality Standards of the Products:
(1) Properties: golden colored and single-particle products; seeds surface was covered with the flesh; tasted sweet and had the characteristic flavor of Siraitiae fructus;
(2) Content of water: no more than 15.0%
(3) Content of mogroside V: no less than 1.0% when calculated based on the dry product weight; and
(4) Directions and dosage: one seed diluted in 50 ml hot water; ready to consume after steeping for 5 minutes.

Embodiment 5

Obtained 100 fresh Siraitiae fructus and removed about 98% of the peel to obtain the flesh masses; put the flesh masses containing the flesh and seeds into an air blowing thermostatic oven, and dried at 60° C. to remove about 20% of water; took out the flesh masses and broke them open lengthways along the Siraitiae fructus to turn the flesh masses into flat sheets materials that contained several rows of seeds; continued to dry at 60° C. to remove about 40% of water; took out and then using the flesh near the peel as the basis for connecting the seeds, separated the tightly attached seeds from the side opposite from the peel; continued to dry at 60° C. until the water content was less than 10.0%; took out and cooled to room temperature, and packaged to obtain final products.

Embodiment 6

Obtained 10,000 fresh Siraitiae fructus and peeled; seeds and flesh were separated by a separating machine; took the seeds to dry at 70° C. until the water content was less than 10.0%; took the flesh to grind into flesh pulp using a grinding machine; then sifted the flesh pulp through a 120-unit silk sieve; added a proper amount of Vitamin C, Hovenia dulcis thumb, and Radix puerariae extract, and homogenized to obtain a flesh mixture; put the dried seeds in a coating pan, heated, and sprayed the pulp onto the seeds and continued to dry until the water content was less than 10.0%; sifted and packaged to obtain the final products.

Embodiment 7

10,000 fresh Siraitiae fructus were peeled; seeds and flesh were separated using a separating machine; seeds were dried at 60° C. until the water content was less than 10.0%; flesh was grinded into pulp using a grinding machine, and sifted the flesh pulp through a 80-unit silk sieve; added a proper amount of Radix puerariae and cortex mori extract, and homogenized to obtain a flesh mixture; put the dried seeds into a one-step granulator, heated, and sprayed the flesh mixture onto the seeds; continued to dry until the water content was less than 10.0%; sifted and packaged to obtain the final products.

Embodiment 8

10,000 fresh Siraitiae fructus were peeled; seeds and flesh were separated using a separating machine; seeds were dried at 60° C. until the water content was less than 10.0%; flesh was grinded into pulp using a grinding machine, and sifted the flesh pulp through a 80-unit silk sieve; added a proper amount of hawthorn extract, and homogenized to obtain a flesh mixture; put the dried seeds into a coating pan, heated, and sprayed the flesh mixture onto the seeds; continued to dry until the water content was less than 10.0%; sprayed a proper amount of ginger extract onto the surface of the products; sifted and packaged to obtain the final products.

Embodiment 9

10,000 fresh Siraitiae fructus were peeled; seeds and flesh were separated using a separating machine; seeds were dried at 60° C. until the water content was less than 10.0%; flesh was grinded into pulp using a grinding machine, and sifted the flesh pulp through a 80-unit silk sieve; added a proper amount of Semen Cassiae and radix polygoni multiflori extract, and homogenized to obtain a flesh mixture; put the dried seeds into a coating pan, heated, and sprayed the flesh mixture onto the seeds; continued to dry until the water content was less than 10.0%; sifted and packaged to obtain the final products.

Embodiment 10

10,000 fresh Siraitiae fructus were peeled; seeds and flesh were separated using a separating machine; seeds were dried at 60° C. until the water content was less than 10.0%; flesh was grinded into pulp using a grinding machine, and sifted the flesh pulp through a 80-unit silk sieve; added a proper amount of Fructus Phyllanthi extract and preservatives, and homogenized to obtain a flesh mixture; put the dried seeds into a high performance coating pan, heated, and sprayed the flesh mixture onto the seeds; continued to dry until the water content was less than 10.0%; sifted and packaged to obtain the final products.

Embodiment 11

10,000 fresh Siraitiae fructus were peeled; seeds and flesh were separated using a separating machine; flesh was grinded into pulp using a grinding machine, and sifted the flesh pulp through a 100-unit silk sieve; added a proper amount of almond and folium eriobotryae extract; seeds were put into a dehumidifying drying device as shown in FIG. 1; turned on the dehumidifying drying device and set relative humidity at 15% and a temperature of 80° C.; an inflow of dry air having relative humidity of 15% and a temperature of 80° C. constantly entered into the drying cabinet to effect the heat exchange and temperature exchange with the Siraitiae fructus seeds; the resulted end air having a temperature lower than 80° C. and relative humidity higher than 15% entered into the dehumidifying drying device, and was dehumidified and dried by the heat generated from operating the device, and continued to dry the Siraitiae fructus seeds; after drying for 5 hours, took out the seeds and separated them; put the seeds into a one-step granulator; temperature of the input air was set at 80° C.; sprayed the flesh pulp onto the boiling seeds, and continued to dry until the water content was less than 10.0%; sifted and packaged to obtain the final products.

Embodiment 12

10,000 fresh Siraitiae fructus were peeled; seeds and flesh were separated using a separating machine; seeds were dried under the sun until the water content was less than 10.0%; flesh was grinded into pulp using a grinding machine, and sifted the flesh pulp through a 80-unit silk sieve; added a proper amount of tea extract and preservatives, and homogenized to obtain a flesh mixture; put the dried seeds into a coating pan, heated, and sprayed the flesh mixture onto the seeds; continued to dry until the water content was less than 9.0%; sifted and packaged the final products into tea bags with each bag containing four seeds.

Embodiment 13

1,000 fresh Siraitiae fructus were peeled; the flesh masses containing flesh and seeds were put in an air blowing thermostatic oven, and dried at 60° C. to remove about 20% of water; took out the flesh masses and broke open the flesh masses lengthways along the Siraitiae fructus, and turned into flat-sheet materials containing several rows of seeds; dried again at 60° C. to remove about 40% of water; took out and cut the flesh masses into single-particle shaped materials, and continued to dry at 60° C. until the water content was less than 10.0%; took out the material and spray-coated chrysanthemum and wild chrysanthemum extract onto the surface; dried at 40° C. until the water content was about 12%; cooled to room temperature and packaged to obtain the final products.

Embodiment 14

200 fresh Siraitiae fructus were peeled; put the flesh masses into a vacuum drying cabinet; removed about 20% of water at 60° C. and a vacuum degree of no more than −0.05 mpa; took out the materials and broke open the seed-containing flesh masses lengthways along the Siraitiae fructus to turn the flesh masses into tile-shaped materials containing several rows of seeds; continued to dry under the same condition to remove about 40% of water; took out and cut the tile-shape flesh masses lengthways into single rows, each row containing 1 to 10 seeds; then using the flesh near the peel as the basis for connecting the seeds, separated the tightly attached seeds from the side opposite from the peel, and turned the material into a row of teeth-like material (similar to the depiction in FIG. 4); continued to vacuum dry under the same condition to reduce the content of water to less than 10.0%; took out the material and cooled to room temperature and packaged to obtain the final products.

Embodiment 15

200 fresh Siraitiae fructus were peeled; air-dried the flesh masses outdoor to remove about 20% of water; broke open the seed-containing flesh masses lengthways along the Siraitiae fructus to turn the flesh masses into tile-shaped materials containing several rows of seeds; put the flesh masses into a vacuum drying cabinet, and dried at 60° C. and a vacuum degree of no more than −0.05 mpa to remove about 40% of water; took out and cut the tile-shape flesh masses lengthways into single rows, each row containing 1 to 10 seeds; then using the flesh near the peel as the basis for connecting the seeds, broke open the tightly attached seeds from the side opposite from the peel, and turned the material into a row of teeth-like material (similar to the depiction in FIG. 4); continued to vacuum dry under the same condition to reduce the content of water to less than 10.0%; spray-coated cinnamon, clove and ginger extract onto the surface of the products; sealed for 8 hours, then sifted and packaged to obtain the final products.

Embodiment 16

10,000 fresh Siraitiae fructus were peeled; seeds and flesh were separated using a separating machine; seeds were put in a microwave drying bed to dry until the water content was less than 10.0%; flesh was grinded into pulp using a grinding machine, and sifted the flesh pulp through a 80-unit silk sieve; added a proper amount of radix notoginseng, radix salvia miltiorrhizae, and Ginkgo biloba leaves extract, and homogenized to obtain a flesh mixture; put the dried seeds into a boiling drying bed, heated, and sprayed the flesh mixture onto the seeds; continued to dry until the water content was less than 10.0%; sifted and packaged to obtain the final products.

Embodiment 17

100 fresh Siraitiae fructus were peeled to obtain flesh masses; flesh masses were dried in the shade to remove about 20% of water; broke open the flesh masses lengthways along the Siraitiae fructus to turn the flesh masses into tile-shaped materials containing several rows of seeds; dried the materials under the sun to remove about 50% of water; separated the tightly attached seeds into single particle shaped materials, and put the materials into an infrared drying bed to dry until the water content was less than 10.0%; took out the materials and cooled to room temperature; sifted and packaged to obtain the final products.

Embodiment 18

1,000 fresh Siraitiae fructus were peeled; the flesh was pressed into thin sheets and dried at 70° C. to remove about 50% of water; the tightly attached seeds were separated and dried at 60° C. to remove about 40% of water; sifted, cooled to room temperature and packaged to obtain the final product.

Embodiment 19

1,000 fresh Siraitiae fructus were peeled to obtain flesh masses; air-dried the flesh masses outdoor to remove about 50% of water; broke open the flesh masses and separated the tightly attached seeds; dried again at 70° C. to remove about 40% of water; took out and cooled the materials to room temperature, and packaged to obtain the final products.

What is claimed is:

1. A method to produce a Siraitia fructus composition comprising:
    a) peeling a Siraitia fructus;
    b) separating the Siraitia fructus flesh and the Siraitia fructus seeds from the Siraitia fructus;
    c) drying said Siraitia fructus seeds at 40° C.-120° C.;
    d) preparing a Siraitia fructus flesh pulp from the Siraitia fructus flesh; and
    e) coating said Siraitia fructus flesh pulp onto the surface of said Siraitia fructus seeds to produce said Siraitia fructus composition, wherein said Siraitia fructus composition contains no more than 10% water.

* * * * *